United States Patent
Sanders

(10) Patent No.: US 6,934,985 B2
(45) Date of Patent: Aug. 30, 2005

(54) COVER

(75) Inventor: Hans-Christian Sanders, Osnabrück (DE)

(73) Assignee: Sanders GmbH, Osnabrück (DE)

(*) Notice: Subject to any disclaimer, the term of this patent is extended or adjusted under 35 U.S.C. 154(b) by 0 days.

(21) Appl. No.: 10/484,663

(22) PCT Filed: Dec. 4, 2002

(86) PCT No.: PCT/EP02/13701
§ 371 (c)(1),
(2), (4) Date: Jun. 30, 2004

(87) PCT Pub. No.: WO03/092451
PCT Pub. Date: Nov. 13, 2003

(65) Prior Publication Data
US 2004/0231055 A1 Nov. 25, 2004

(30) Foreign Application Priority Data
May 2, 2002 (DE) .......................... 102 19 702

(51) Int. Cl.⁷ ................................................ A47G 9/02
(52) U.S. Cl. ................................ 5/482; 5/413 R; 5/502
(58) Field of Search ..................... 5/482, 502, 413 R, 5/500, 486

(56) References Cited

U.S. PATENT DOCUMENTS

| 2,808,596 | A |   | 10/1957 | Schreiner |       |
|-----------|---|---|---------|-----------|-------|
| 3,199,123 | A | * | 8/1965  | Komiske   | 5/502 |
| 3,325,832 | A | * | 6/1967  | Malicki   | 5/487 |
| 3,840,923 | A | * | 10/1974 | Bos       | 5/499 |
| 4,324,012 | A |   | 4/1982  | Cannaday  |       |
| 4,525,406 | A |   | 6/1985  | Pollock   |       |
| 4,839,934 | A |   | 6/1989  | Rojas     |       |
| 5,181,287 | A |   | 1/1993  | Yang      |       |
| 5,386,602 | A |   | 2/1995  | Krenzler  |       |
| 5,669,088 | A |   | 9/1997  | McNamee   |       |
| 6,615,427 | B1 | * | 9/2003 | Hailey    | 5/495 |

FOREIGN PATENT DOCUMENTS

| CH | 478552        | 3/1969  |       |
|----|---------------|---------|-------|
| CH | 682 977 A     | 12/1993 |       |
| DE | 887 562 C     | 8/1953  |       |
| DE | 198 28 218 A1 | 12/1999 |       |
| DE | 201 02 560 U1 | 8/2002  |       |
| EP | 0 673 613 A1  | 9/1995  |       |
| GB | 486763 A      | 6/1938  |       |
| GB | 859071        | 1/1961  |       |
| GB | 2 266 661 A   | 11/1993 | 5/502 |
| GB | 2 295 543 A   | 6/1996  |       |
| WO | WO 92/18036   | 10/1992 |       |

* cited by examiner

Primary Examiner—Alexander Grosz
(74) Attorney, Agent, or Firm—Scully, Scott, Murphy & Presser

(57) ABSTRACT

A cover of a conventional type, in particular for beds, which has at least one flexible layer of a light, insulating material and which is designed to the desired heat retention in the bed, is equipped in view of an improved moisture regulation and a dissipation of the moisture released by the body as well as excess heat in such a manner that the layer is provided with ventilation openings.

12 Claims, 7 Drawing Sheets

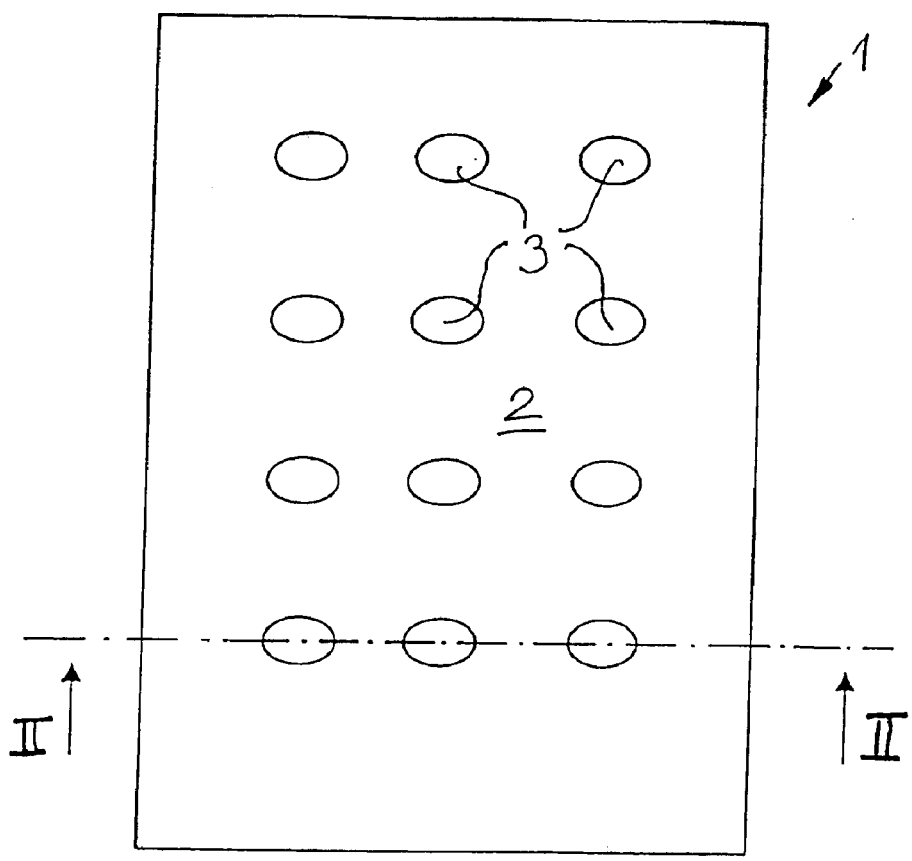
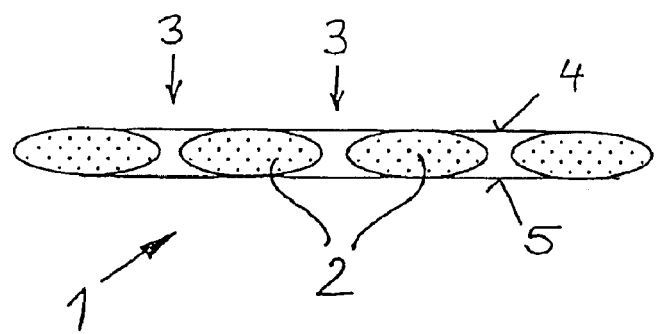
FIG. 1
FIG. 2

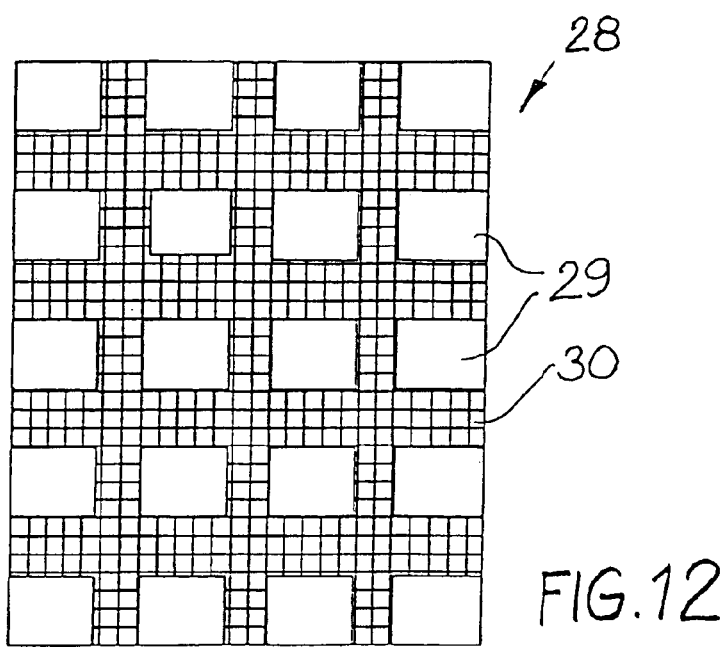
FIG. 12
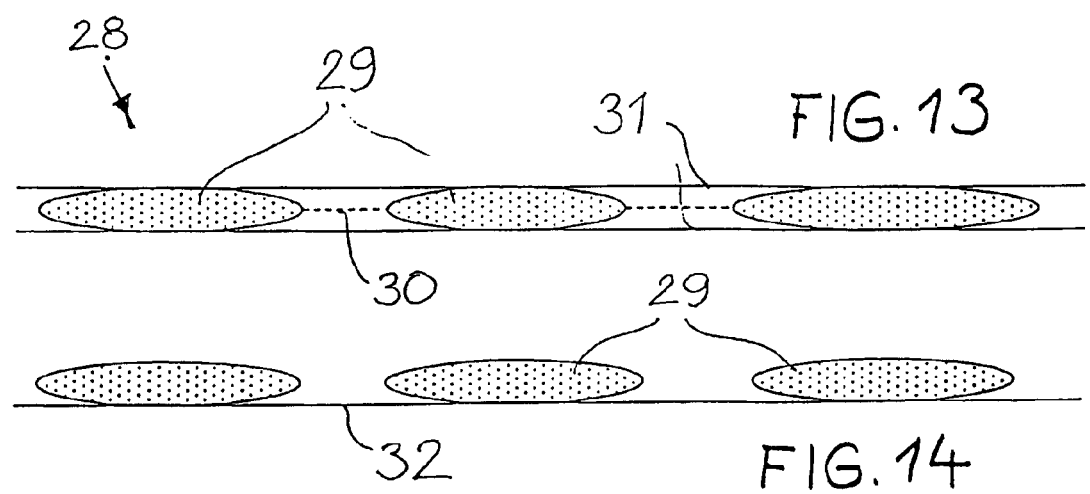
FIG. 13
FIG. 14

COVER

BACKGROUND OF THE INVENTION

The invention relates to improvements in covers, particularly in connection with bed covers which incorporate at least one flexible layer of a light, insulating material.

Covers, as provided particularly for beds but also for other furniture, should be light and flexible, i.e. pliant, so as to be able to sufficiently adapt to the body, while considering the thermal characteristics regarding ambient temperature, e.g. in particular the bedroom temperature at night, such that a more or less "warm" cover is selected. Accordingly, as a rule, in southern countries, the covers regularly only consist of a wool blanket over a simple sheet, which is supplemented by a second wool blanket or further wool blankets when the ambient temperature is colder. In middle and northern Europe, covers are predominantly used in which one layer of light, insulating material consisting of a quilted cover or a down comforter is entirely enclosed by a cover casing. It is also possible to select between thicker or better insulating layers and thinner layers, so as to take the ambient temperature into account. The following consideration is also true for special forms of covers, in particular also for sleeping bags, which are to be included in the term "cover".

However, it has been shown that a satisfactory resting or sleeping climate can possibly be obtained therewith only to an insufficient extent. During sleep or rest, the vapour permeability of the cover and the ambient humidity of the air may result, depending on the perspiration of the person lying down, in a general or partial body perspiration which is unpleasant both when feeling cool or warm. Apart therefrom, damp bedclothes are also a health hazard if the person becomes uncovered and a local cooling should accidentally occur.

During the night, human beings sweat out up to approximately 500 ml of water. This water or water vapour must leave the entire bed system so as to avoid moisture accumulation in the space taken up by the sleeper under the covers. Dissipation may either be downwardly through the support system, such as the mattress, or through the cover or lateral openings when the body is not completely surrounded.

It is known that the main portion of moisture must be transported off through the cover. However, the moisture meets with various resistances here, i.e. initially the first layer of the cover casing, then the first layer of the cover ticking, then the filler material, then the second layer of the cover ticking, the second layer of the casing and only then reaches the ambient air. While passing these layers, both a storage of moisture, which must again be transported further and discharged, and a mixture of diffusive and slightly convective transportation takes place. As a whole, however, this constitutes slow, moisture-equalizing processes, each of which quasi including high individual resistances. Last but not least, the development of cover tickings for down or fiber covers as well as covers filled with natural hair or animal hair in the direction of a corresponding down or fiber density, and thus textiles having a high fiber density and fine individual fibers, which naturally have a high density as regards a piercing of the individual filler media, but which clearly also provide reduced air permeation. This leads to a reduction of the overall exchange of air containing moisture, and to a kind of congestion. The consequence is—and this is also shown in studies by different institutes—that a quasi tropical climate is obtained within the space under the cover. The air temperatures roughly range between 30 and 35° C. with a correspondingly high air humidity.

DISCUSSION OF THE PRIOR ART

However, since human beings do not feel comfortable at such temperatures, this results in that sleep becomes easy, and the sleeper tosses in bed and uncovers himself. After this uncovering, an evaporation-cooling of exuded perspiration occurs, however, i.e. a cooling-down which results, in turn, in that the sleeping person will again cover himself.

As a result, uneasy sleep phases occur disturbing the normally restful sleep cycle of a sleeper.

It is therefore the object of the invention to provide a cover which is suited to avoid problems not only regarding thermal characteristics, i.e. sufficient insulation and dissipation of excess heat, but also regarding moisture transportation, in particular for human beings having the tendency to sweat, or in a muggy room climate, with the handling, use, cleaning and the like being able to be carried out in a known manner, and with the production costs also remaining within an acceptable range.

In accordance with the invention, this object is solved with a cover having at least one flexible layer consisting of a light, thermally insulating material. This cover provides ventilation possibilities for the transportation of air through the cover and thereby also allows a moisture compensation from the body to the environment as well as dissipation of excess heat (heat accumulation). The cover as a flexible layer of light, insulating material can be a simple wool blanket with or without an additional sheet or casing, it may also be a quilted cover or a down comforter. It is essential that it is not a closed layer obstructive for air flow and that it nevertheless maintains a predetermined thermal insulation.

The invention is therefore based on the concept of utilizing ventilation openings, in the cover which ensure both a direct of updraft the mark air and, thus, guarantee a high dissipation of the air humidity, and further a forced convection with body movements, and thus allow volume changes in the space under the cover, but which nevertheless maintain the known properties of pliancy and comfort. This is achieved by all means with known filling media, so that even in the summer very soft, comforting cover constructions are possible which nevertheless create an ideal climate in the space taken up by the sleeper under the cover. This, in turn, results in a calmer sleeping behavior and better temper and productivity as well as, possibly, in an improved health of the sleeping person.

With this type of cover and with an adapted constructive embodiment, the main portion of the exuded body moisture is passed via the opening systems and, thus, the cover itself is burdened to a far lesser extent by water-vapour transportation. This has the effect that the feeling no longer arises of a clammy bed, as it is colloquially known, and that less time will be needed to air the bed cover.

The sleeping practice to be also considered for comparison purposes, for instance that a person sleeps only under a sheet or a cover casing in hot or muggy weather, is less advantageous as compared therewith, since the heat insulation is lost for the most part when a sheet lies on the body, without this, however, allowing a correspondingly easy transition of the air to the outside.

The ventilation openings of the cover according to the invention can be spanned by wide meshwork or a coarse-meshed material so as to ensure the cohesion of the cover also particularly if there are larger or longitudinally extended openings. The flexible layer of insulating material, e.g. in the form of a wool blanket or also a quilted cover or down comforter, can indeed be combined with a sheet or a cover casing, in particular for hygienic reasons, if an essentially facilitating air transition still results through the ventilation openings, especially since such sheets or cover casings are generally not made of particularly dense textiles such as, for instance, ticking fabric. Such a cover casing then spans the ventilation openings in the form of a meshwork. The permeability of such a spanning construction is essential to ensure on the one hand the desired ventilation and on the other to avoid those effects occurring when lying partially uncovered.

In connection therewith, it has been shown to be advantageous when the permeability of the meshwork ranges from 200 l/dm$^2$·min at a pressure gradient of 200 Pa to 9000 l/dm$^2$·min at a pressure gradient of 13 Pa, which contrasts the mesh both from fabrics having a greater density and from free openings. In order to fulfil the light covering function, the "meshwork" may have various forms. Textiles can be found preferably in the field of knit fabrics such as open-work knit fabics, in particular polyester open-work knit fabrics, or charmeuse goods such as rhombus charmeuse or open-work charmeuse. Gauze or mesh fabrics from the field of textiles represent suitable meshwork. Further, textile, open-measured material come under consideration, such as non-woven materials, in particular thermo-bonded spun non-woven materials, having optionally cut-out holes or fibers in biaxial or multiaxial layers as are used as reinforcement material in fiber-reinforced synthetics. When looked at from above or looked through, advantageous examples of meshworks can be observed having a proportion of openings such as holes, pores, free mesh space and the like of 15 to 30%.

The effect of the meshwork as in a predeterminable permeability of the ventilation openings may further be supplemented by additional filler of fibrous material or light, open bulk material or fillers or open-pored flexible bodies, in particular foam material having large pores, which are arranged on one side so as to form a single meshwork, or are arranged preferably between two meshwork layers. They are then virtually a part of a spatial meshwork.

The ventilation openings preferably have a width of 5 to 300 mm, also depending on a thickness of the cover they may have a width of 0.3 to 150 mm. In connection therewith, the ventilation openings should occupy an aerial proportion ranging from 3 to 50%, preferably 5 to 20%, of the entire area of the bed.

BRIEF DESCRIPTION OF THE DRAWINGS

Several embodiments of the invention are shown in the drawings and are described in detail below. In the drawings are shown:

FIG. 1 a view of a cover having ventilation openings distributed in the form of a grid;

FIG. 2 a sectional view taken along line II—II in FIG. 1;

FIG. 12 a cover made of a plurality of cushion-like layer parts on a meshwork;

FIG. 13 a sectional view taken through the cover according to FIG. 12, shown on an enlarged scale;

FIG. 14 a cross-section through a cover modified over FIG. 13;

DETAILED DESCRIPTION OF THE INVENTION

Figure 3:
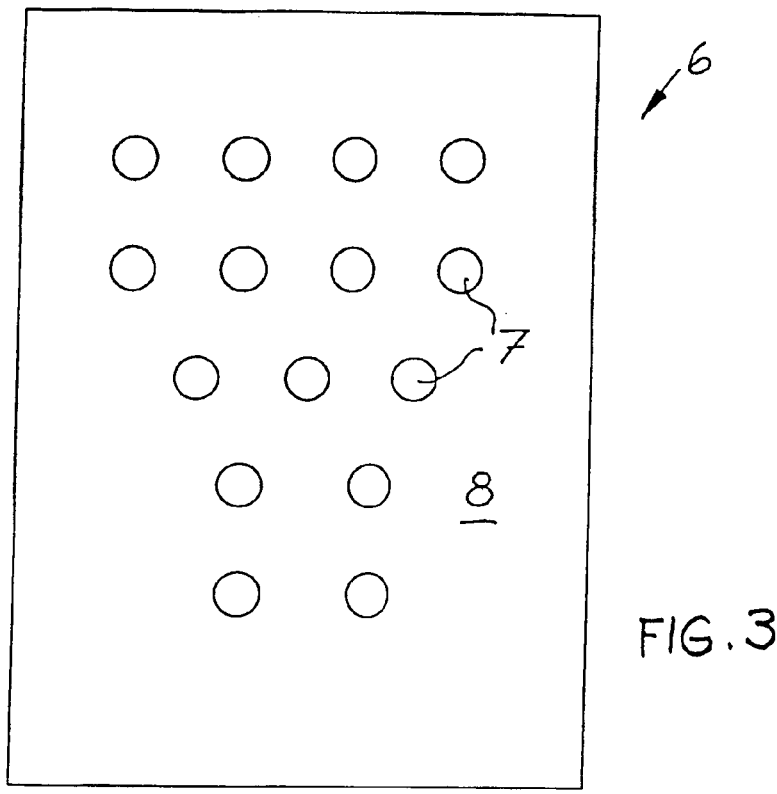
FIG. 3 a cover having an uneven distribution of ventilation openings.

The cover designated throughout FIGS. 1 and 2 by reference numeral 1 comprises a large, continuous, flexible layer 2 of a light, insulating material, perforated by oval or round holes 3 distributed in a grid. The layer 2 can e.g. be observed like a down comforter having a ticking upper plate 4 and a lower plate 5, between which a filling of fiber, natural hair, animal hair or down is enclosed. This layer of a light, insulating material may also be provided with a reflecting layer or filler which is responsible, for instance, with a fine fiber metallization for a screening against electromagnetic pollution. However, the direct influence of the reflecting portion on the bed climate is the result of a retention of heat radiation. The reflection in the infrared range improves and equalizes the insulating effect of the layer 2. The ventilation openings 3 simultaneously adopt the function of a connection and a spacing between the upper plate 4 and the lower plate 5, which is otherwise mostly obtained by ribs.

The essential novel effect is obtained by the ventilation openings 3 which allow an air exchange between the two sides of the cover 1 and thereby allow the dissipation of the air having a high proportion of body moisture from below the cover. This is already possible due to the updraught of warm air, but this is particularly possible when the person resting below the cover 1 moves and the spaces below the cover are thereby altered.

For a maximum air exchange, the cover 1 may to a large extent be kept free in the area of the ventilation openings 3. However, in principle, an air exchange is also possible by means of conventional textile slip materials, as are used for fitted sheets or cover casings. These slip materials represent meshworks along the lines of the invention which regulate the ventilation by means of the ventilation openings.

A cover 6 according to FIG. 3 has unevenly distributed ventilation openings 7 which roughly reflect a distribution of the body masses or body surfaces of a resting person and which are particularly adapted to the varying requirements for air exchange which is different depending on the area. These ventilation openings 7 are again incorporated into a layer 8 of a light insulating material or a material of a conventional kind.

Figure 4:
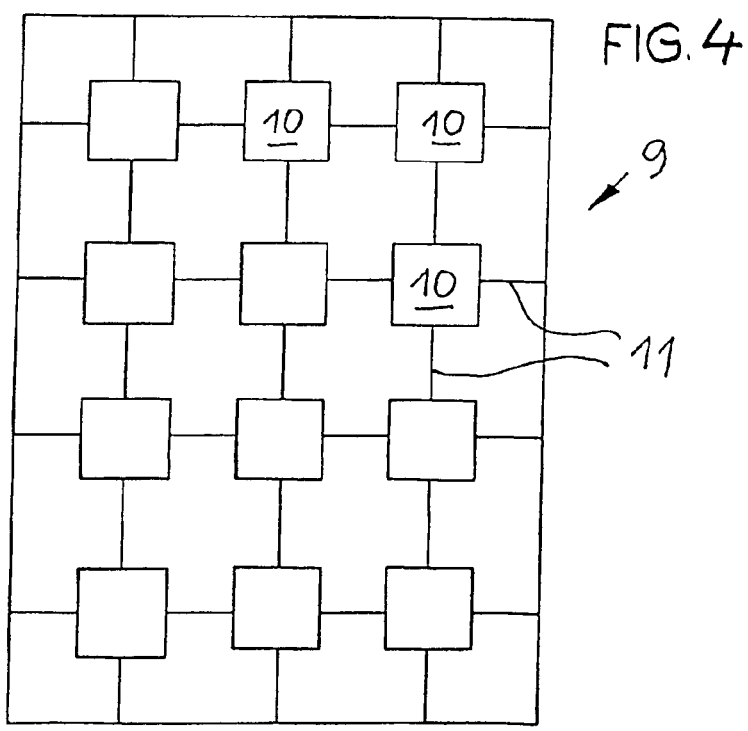
FIG. 4 a cover quilted in squares having ventilation openings.

A cover 9 according to FIG. 4 is provided with regularly distributed, rectangular ventilation openings 10 which are incorporated in a grid system in a cover, in particular a down comforter, divided by ribs 11.

Figure 5:
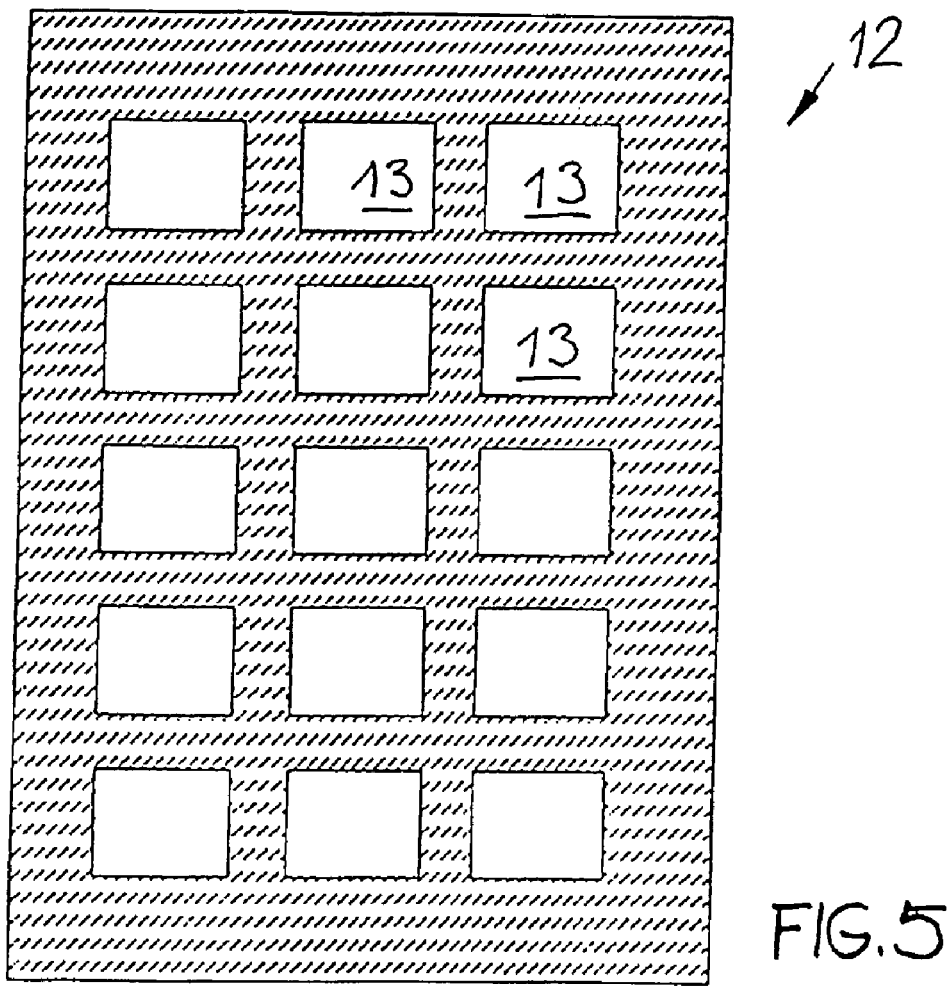
FIG. 5 a cover having rectangular ventilation openings spanned by meshwork.
Figure 6:
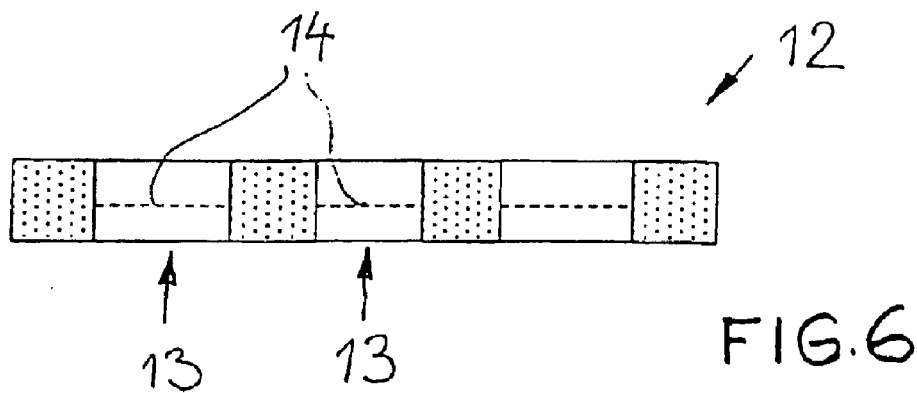
FIG. 6 a cross-section through the cover according to FIG. 5.

A cover 12 according to FIGS. 5 and 6 having (for example) rectangular ventilation openings 13 is, in turn, to be regarded starting with any conventional cover as being amended by the ventilation openings 13, with the ventilation openings 13 being each spanned by a meshwork 14 such that the cohesion of the cover 12 is not lost due to the openings and such that the cover still provides optically a self-contained appearance. Such a meshwork may be designed as a rough fabric, however, it may also consist of a perforated flat material of fabric, knit fabric, sheets or the like. Particularly suited are commercially available open-work knit fabrics, whose holes and hole proportions must be provided in a form large enough for the desired permeability. The mesh-like coverings, however, provide a suitable passage for ventilation.

Figure 7:
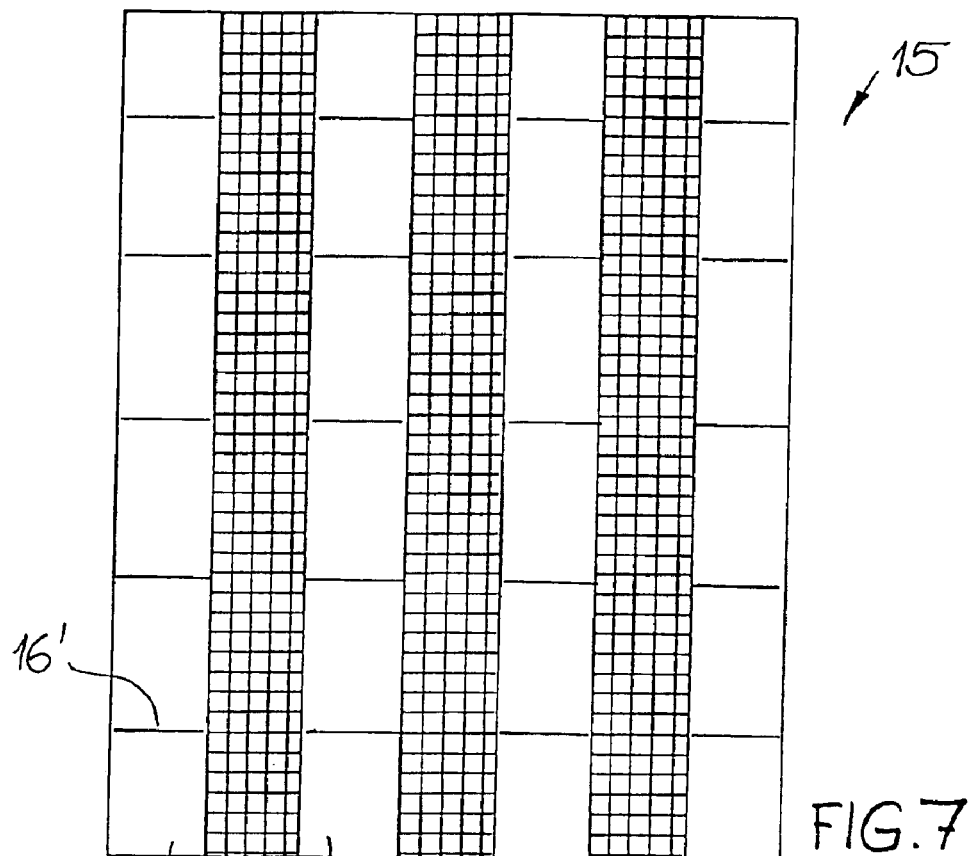
FIG. 7 a cover having strip-like ventilation openings.
Figure 8:
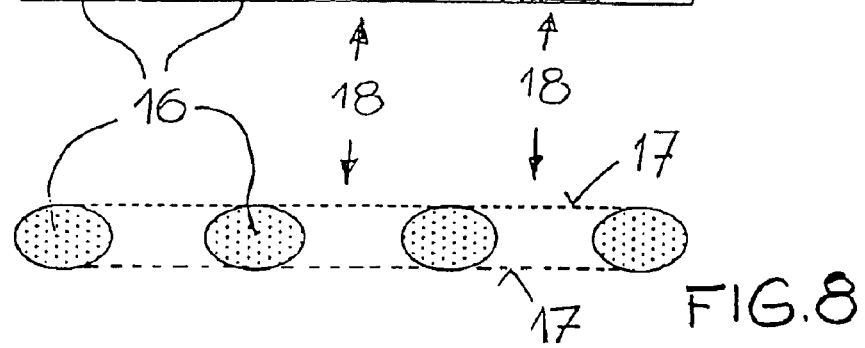
FIG. 8 a cross-section through the cover according to FIG. 7.

A cover 15 according to FIGS. 7 and 8 is formed of strip-like layers 16 of insulating material having cross-quilt seams 16' which are defined at predetermined distances by continuous meshwork 17, such that ventilation openings 18 are formed which have likewise the form of strips. It is appreciated that normally relatively narrow ventilation openings ensure sufficient permeability, so that the proportions as shown are only considered in exceptional cases. Such an embodiment can be efficiently manufactured from the strips using the "element structure".

Figure 9:
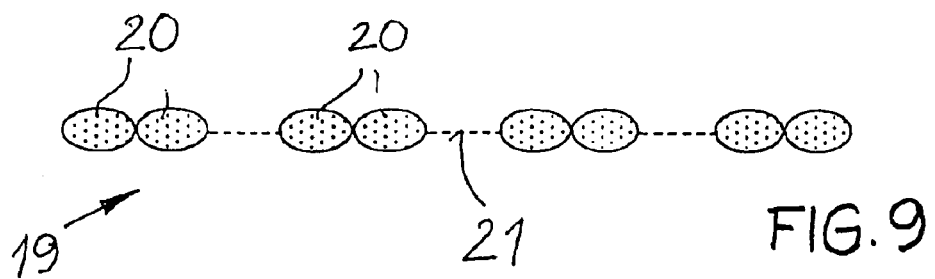
FIG. 9 a cross-section through a cover modified over FIG. 8.

The cross-sectional drawing according to FIG. 9 shows a cover 19, in which the insulating material is present each as double strips 20, between which strips 21 of a meshwork having wide openings are responsible for spacing fixation and ventilation.

Figure 10:
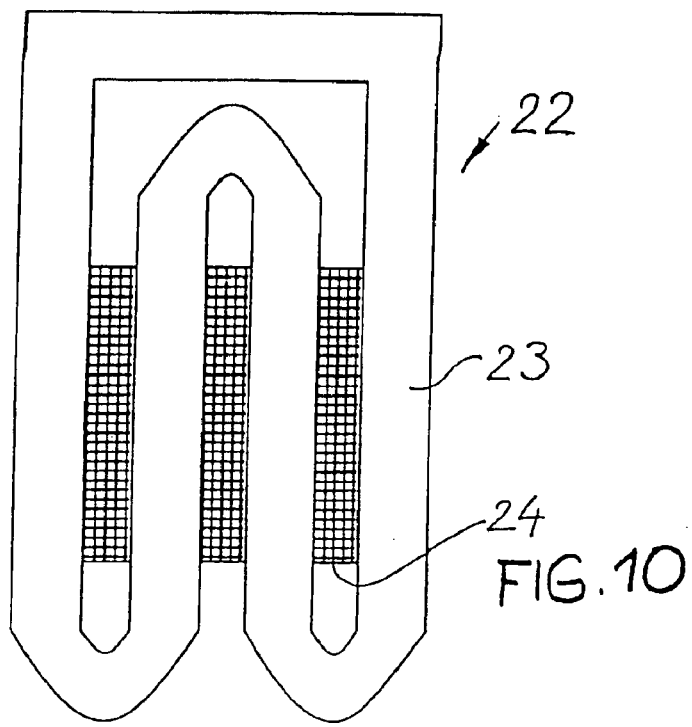
FIG. 10 a cover having a layer formed of a longitudinal strip of insulating material, which is fixed by a mesh network.

One further development of a cover 22 according to FIG. 10 having a single strip 23 of insulating material laid as a sinuous line is fixed in the "paperclip" shape by a rough-meshed meshwork 24 which extends in a middle area traversely over the twists.

Figure 11:
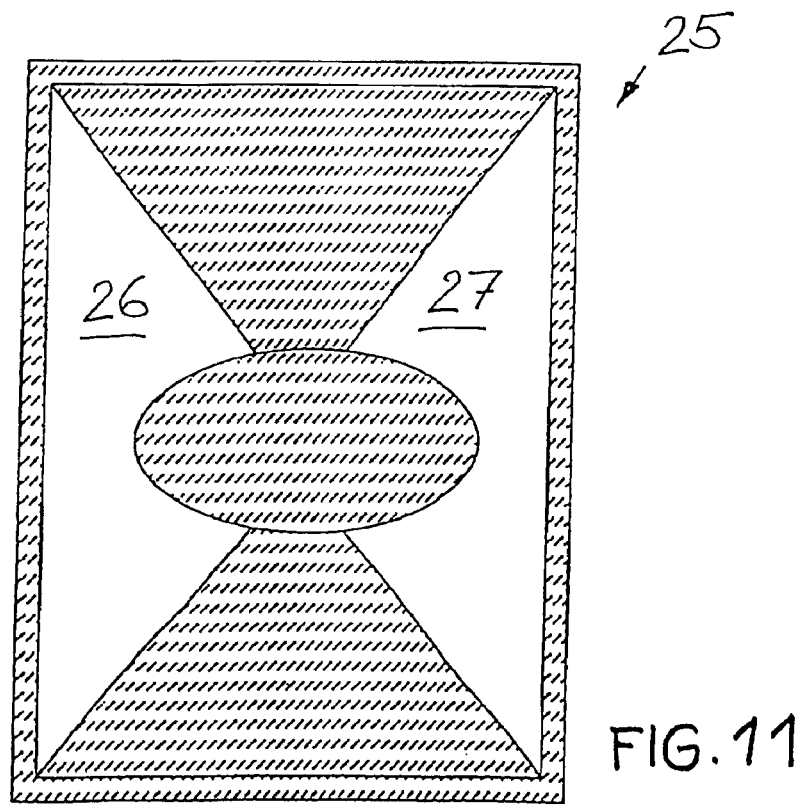
FIG. 11 a cover having lateral ventilation openings.

In FIG. 11, a cover 25, which, starting from a rectangular shape, is reduced by large ventilation openings 26, 27 on both sides at mean regions, for example, to a diabolo shape, which allows to satisfy both the remaining heat requirement of the user but also a good ventilation via the openings on both sides, also extending traversely through the openings 26 and 27. The permeability of this cover 25, as well as that of the cover 22, may be predetermined e.g. by a cover casing (not shown).

A cover 28 according to FIG. 12 consists of a layer of insulating material fragmented into rectangular elements 29 which are connected by a net 30 of a meshwork lying therebetween. The elements 29 are, for example, cushions of any known filling. The entire cover 28 may be enclosed in a cover casing 31, as indicated in the cross-sectional drawing according to FIG. 13.

One alternative possibility according to FIG. 14 is the connection of the individual cushions 29 at the predetermined distance by a common meshwork 32.

In all of the above-described cases, a conventional cover designed for a desired insulation with ventilation openings can be aerated in an enhanced manner such that the dissipation of moisture is no longer ascribed solely to the absorbency and moisture transportation of the textiles and fillers, to the contrary, a ventilation results, particularly during body movements, with which the more humid air near the body is exchanged for absorptive ambient air. If body moisture is also absorbed in a conventional manner by the layer of insulating material, the discharge to the ambient air is then carried out not only through the (upper) side of the cover facing away from the body, but also traversely to the ventilation openings. The insulating material—for instance feathers or fibers—can therefore be kept dryer.

Figure 15:
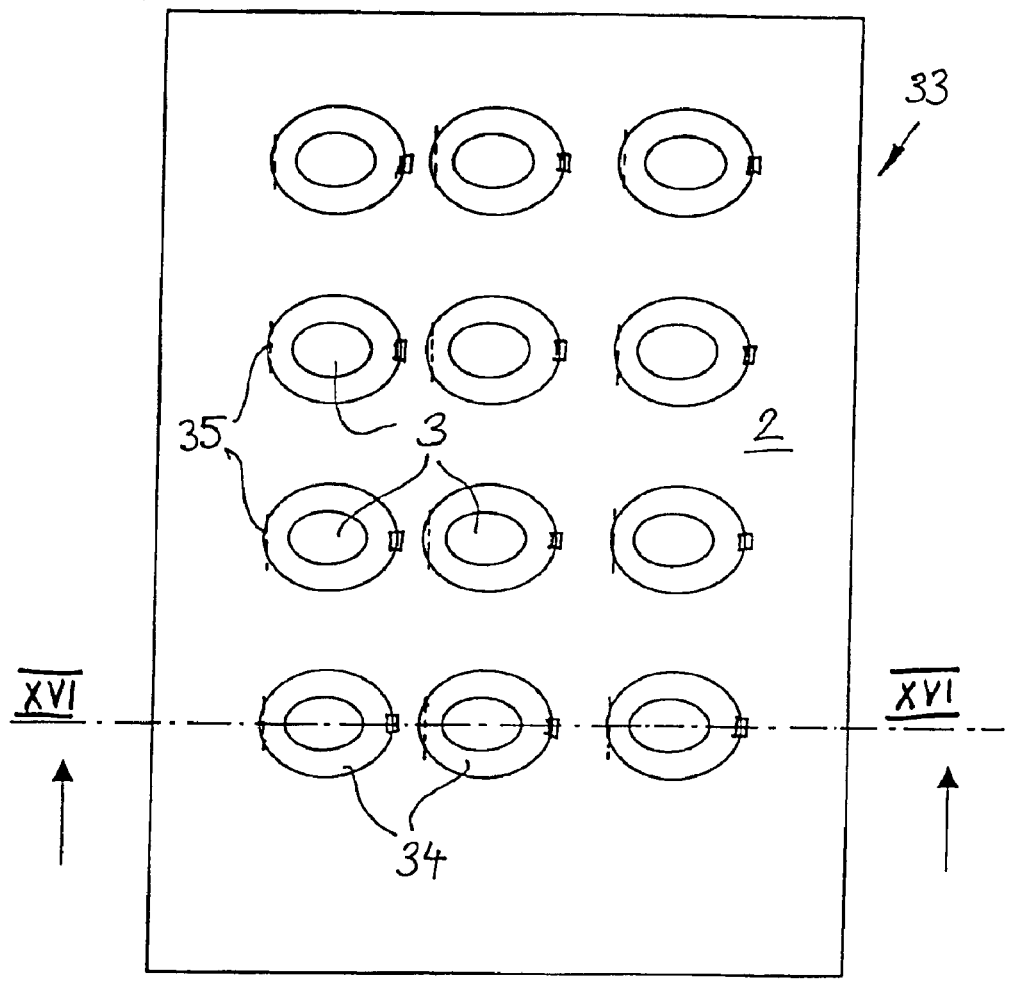
FIG. 15 a cover having closing caps for ventilation openings.
Figure 16:
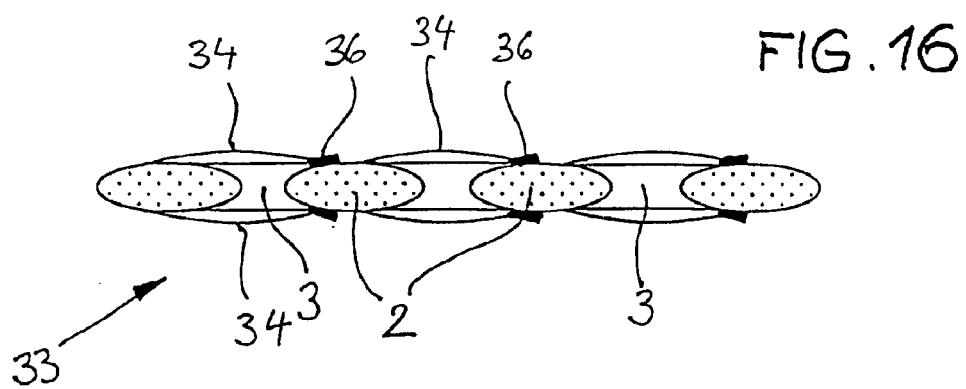
FIG. 16 a cut along line XVI—XVI of FIG. 15.

In addition to this, according to an embodiment shown in FIGS. 15 and 16, an optional possibility of closing the ventilation openings is provided. A cover designated as a whole as 33 has a layer 2 of insulating material having ventilation openings 3 which can concur with those of FIGS. 1 and 2 and which are therefore designated by the same reference numerals. As compared with the cover 1 of FIGS. 1 and 2, the cover 33 is provided with closing flaps 34, which are fixed each in an edge area by a seam 35 on the layer 2 at one side of the ventilation opening 3, and which have at least one bonding fastener 36 at the opposite edge, with which they are to be detachably fixed to the layer 2 and thereby cover the ventilation opening 3. The bonding fastener is e.g. a hook-and-loop fastener or an adhesive fastener. Other fasteners, such as buttons or snaps, are principally also possible, but they are not preferred due to the formation of hard punctiform surface spots. The closing flaps preferably consist of textile material, i.e. of strong ticking fabric, and block the ventilation openings 3 if the cover appears to be too cool in wintertime or if perspiration is desired, for instance, for health reasons. As shown, the closing flaps 34 may be arranged both on the upper side and on the lower side of the layer 2, so that the ventilation openings can not only be blocked but can be converted to air chambers which provide an even higher insulating effect.

A cover may, of course, have a plurality of layers of insulating material, so as to provide the insulating effect like the conventional covers without ventilation openings of known "duo covers", by the number of layers respectively used and—with layers of varying thickness or different insulation properties—by the selection of the layers. These layers may then be sewn together, e.g. at the edges, be buttoned together or fixed to each other by a bonding fastener. They may also be held together by a cover casing.

These variation possibilities may also be applied to the covers according to the invention, with there being the additional possibility that the ventilation openings may be brought to overlap between the layers in order to achieve as great a ventilation as possible, or to more or less close the ventilation openings by an offset between the layers, or to provide, when there is an offset between the layers, a longer path through the ventilation openings. Such an offset may be obtained by bonding means, such as hook-and-loop fasteners. Several lines of buttons or buttonholes may also allow an optional offset. Also, if the layers of a cover converge, an offset may e.g. be obtained by twisting a layer by 180 degrees if the ventilation openings are distributed on each layer asymmetrically or not point-symmetrically.

For quilted covers, in which the upper and lower plates are generally sewn together along the quilting seam (without spacing ribs), correspondingly flat ventilation openings are obtained due to the manufacturing process, in particular if a flat or non-voluminous filler material is used. In order to obtain ventilation openings also here which have a passage length in which the air moves in principle freely but calmly or slowly and is therefore maintained at a given volume, multilayered, in particular duo-layered quilted covers having separated ventilation openings have been shown to be advantageous, with chambers being formed therebetween in which an air volume is maintained.

The advantages of a cover can also observed—actually surprisingly—in pillows in which the ventilation openings generally run traversely through the pillow only to a mattress or a like support, but which nevertheless still provide good ventilation due to the traverse connections and movements.

What is claimed is:

1. A cover in particular for beds, having at least one flexible layer of light insulating material, characterized in that the layer is provided with ventilation openings each of which is spanned by a separate meshwork, said flexible layer having a ticking upper sheet and a lower sheet between which sheets there is enclosed a filling selected from the group of materials consisting of fibers, natural hair, animal hair or down; and wherein said meshwork has a permeability within the range of about 200 $1/dm^2$.min. at a pressure gradient of 200 Pa to about 900 $1/dm^2$ min. at a pressure gradient of 13 Pa.

2. Cover according to claim 1, characterized in that said cover is formed as a sleeping bag.

3. Cover according to claim 1, characterized in that the ventilation openings are arranged in a grid pattern.

4. Cover according to claim 1, characterized in that the ventilation openings are formed in the shape of strips.

5. Cover according to claim 1, characterized in that the ventilation openings are formed in the shape of intermediate spaces between strip-like or cushion-like elements of the insulating layer.

6. Cover according to claim 1, characterized in that the ventilation openings are unevenly distributed.

7. Cover according to claim 6, characterized in that the distribution or the shape of the ventilation openings is oriented to the zones of the human body.

8. Cover according claim 1, characterized in that said cover has a plurality of layers.

9. Cover according to claim 8, characterized in that the ventilation openings of the layers are offset from each other.

10. Cover according to, claim 1, characterized in that the at least one layer includes a material which reflects electromagnetic radiation.

11. Cover according to claim 1, characterized in that closing flaps are associated at least in part with the ventilation openings.

12. Cover according to claim 11, characterized in that the closing flaps consist of textile material and are fixed with bonding fasteners.

* * * * *

UNITED STATES PATENT AND TRADEMARK OFFICE
CERTIFICATE OF CORRECTION

PATENT NO. : 6,934,985 B2
DATED : August 30, 2005
INVENTOR(S) : Hans-Christian Sanders It is certified that error appears in the above-identified patent and that said Letters Patent is hereby corrected as shown below:

Column 7,
Line 10, "900" should read -- 9000 --.

Signed and Sealed this

Seventh Day of February, 2006

JON W. DUDAS
*Director of the United States Patent and Trademark Office*